United States Patent [19]

Bell et al.

[11] 4,412,995
[45] Nov. 1, 1983

[54] PENTACYCLIC PHENYLPYRAZOLE COMPOUNDS AS ANTI-INFLAMMATORY AGENTS

[75] Inventors: Malcolm R. Bell, East Greenbush; John L. Herrmann, Jr., Kinderhook, both of N.Y.

[73] Assignee: Sterling Drug Inc., New York, N.Y.

[21] Appl. No.: 339,116

[22] Filed: Jan. 13, 1982

Related U.S. Application Data

[63] Continuation-in-part of Ser. No. 236,215, Feb. 19, 1981, abandoned.

[51] Int. Cl.[3] .................. A10K 31/505; C07D 231/54; C07D 491/20
[52] U.S. Cl. .................................... 424/251; 544/231; 548/371; 568/328
[58] Field of Search ........................ 544/231; 424/251

[56] References Cited
PUBLICATIONS

Fried et al., J. Am. Chem. Soc. 85, 236–238 (1963).

*Primary Examiner*—Mark L. Berch
*Attorney, Agent, or Firm*—Thomas L. Johnson; B. Woodrow Wyatt

[57] ABSTRACT

Compounds of the formula

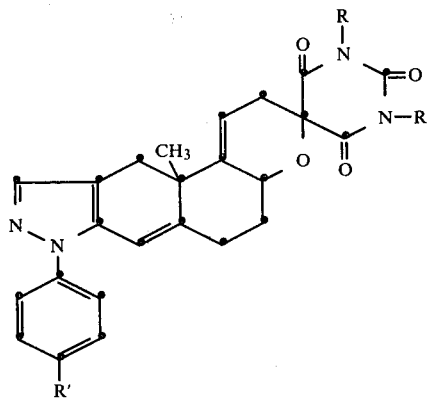

where R is hydrogen, methyl, ethyl, propyl, 2-propenyl or 2-propynyl; and R' is hydrogen or fluoro possess anti-inflammatory activity. The compounds where R is H are prepared by reacting a compound of the formula

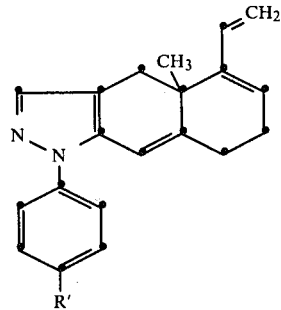

with (1H,3H)-pyrimidine-2,4,5,6-tetrone. The compounds where R is other than hydrogen are prepared by reacting a compound where R is hydrogen with the appropriate alkylating agent.

12 Claims, No Drawings

PENTACYCLIC PHENYLPYRAZOLE COMPOUNDS AS ANTI-INFLAMMATORY AGENTS

This application is a continuation-in-part of application Ser. No. 236,215, filed Feb. 19, 1981, now abandond.

BACKGROUND OF THE INVENTION (1) Field of the Invention

The present invention relates to novel polycyclic fused pyrazole compounds, their use as anti-inflammatory agents, and a method of preparation thereof.

(2) Description of the Prior Art

Typical glucocorticoid activity is rarely found in structures which do not possess an intact steroid nucleus. Such activity is found in naturally occurring steroids such as cortisone, hydrocortisone and aldosterone, as well as numerous synthetic modifications thereof, all containing the intact steroid nucleus. An example of a synthetic cortical steroid having high activity is a fluorophenylpyrazole derivative reported by Fried et al., J. Am. Chem. Soc. 85, 236 (1963), having the structure

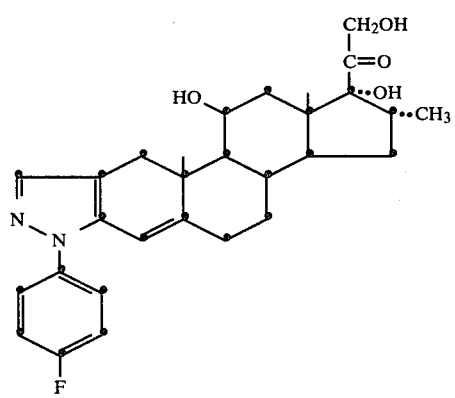

SUMMARY OF THE INVENTION

In a product aspect, the invention relates to compounds having the formula:

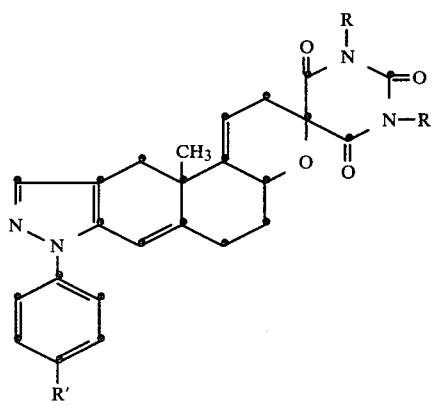

where R is selected from the group consisting of hydrogen, methyl, ethyl, propyl, 2-propenyl and 2-propynyl; and R' is selected from the group consisting of hydrogen and fluoro.

In a further product aspect, the invention relates to a pharmaceutical composition for treating inflammation in mammals which comprises an anti-inflammatorily effective amount of a compound of formula I and a pharmaceutically acceptable carrier.

In a process aspect, the invention relates to a process for preparing the compound of formula I where R=H by reacting 1-ethenyl-6-(4-R'-phenyl)-3,4,9,9a-tetrahydro-9a-methyl-6H-naphtho[2,3-c]pyrazole of the formula:

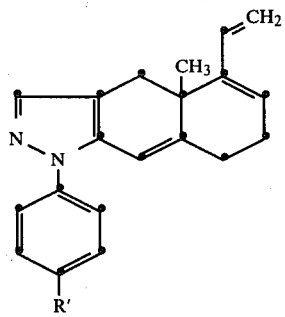

with (1H,3H)-pyrimidine-2,4,5,6-tetrone of the formula

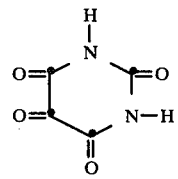

In a further process aspect, the invention relates to a process for preparing a compound of formula I where R is other than hydrogen, which comprises reacting the compound of formula II with (1H,3H)-pyrimidine-2,4,5,6-tetrone, and reacting the resulting compound of formula I where R is hydrogen with an alkylating agent of the formula R-X where R is other than hydrogen and X is halogen in the presence of a strong base.

In a still further process aspect, the invention relates to a method of reducing inflammation in a mammal which comprises administering to said mammal an anti-inflammatorily effective amount of a compound of formula I.

DETAILED DESCRIPTION INCLUSIVE OF PREFERRED EMBODIMENTS

The novel intermediates of formula II are prepared from a known starting material, 5-ethenyl-4,4a,7,8-tetrahydro-4a-methyl-2(3H)-naphthalenone (cf. Bell et al. U.S. Pat. No. 4,157,349, June 5, 1979) in accordance with the following reactions:

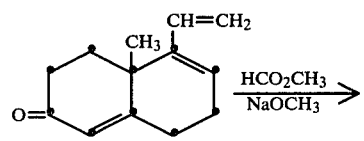

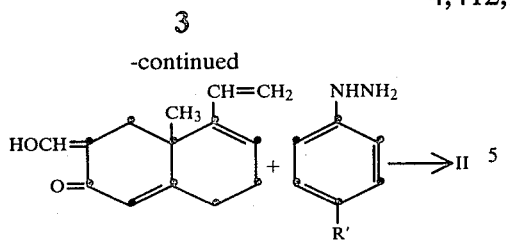

The trienone starting material is reacted with methyl formate in the presence of sodium methoxide in an inert solvent such as tetrahydrofuran to afford 5-ethenyl-3-hydroxymethylene-4,4a,7,8-tetrahydro-4a-methyl-2(3H)-naphthalenone, and the latter is then reacted with phenylhydrazine or 4-fluorophenylhydrazine or an acid-addition salt thereof in the presence of acetic acid to give a compound of formula II.

In the preparation of the compound of formula I where R=H by reacting a compound of formula II with (1H,3H)-pyrimidine-2,4,5,6-tetrone, the reaction takes place by heating the reactants in an inert solvent at a temperature between about 50° and 150° C.

In the preparation of a compound of formula I where R is other than hydrogen by reacting a compound of formula I where R is hydrogen with an alkylating agent, RX, the reaction takes place in the presence of a strong base such as sodium hydride, sodium methoxide, sodium amide, or the like, in an inert solvent under essentially anhydrous conditions. The reaction takes place at ambient temperatures.

The compounds of formula I exhibit a biological profile characteristic of compounds possessing glucocorticoid properties and systemic and/or topical anti-inflammatory activity; cf. R. H. Silber, The Biology of Anti-inflammatory Steroids, Annals of the New York Academy of Sciences, Vol. 82, Art. 4, pp. 821-828.

When the compounds of formula I having systemic endocrinological activity are administered orally to rats they cause a significant depression in thymus weight, adrenal weight and body weight gain without a change in food consumption.

The compounds of formula I where R is hydrogen or methyl and R' is fluoro have also been found to possess oral glucocorticoid activity by the liver glycogen deposition test and anti-inflammatory activity by the α-tocopherol pouch test in rats.

The compounds of formula I (R and R'=H) and (R=$CH_2CH_2CH_3$, R'=F) do not demonstrate systemic endocrinological activity but are active topically (locally) in the cotton pellet granuloma assay.

The test procedures used to determine the biological activities of the compounds of the invention were carried out as follows:

Endocrine Profile:

Mature female rats with an average body weight of 202 g and a body weight range of 15 g or less were medicated orally with test compound for 2 weeks. The test compound was prepared as a solution or suspension in 1% gum tragacanth or 0.75% methyl cellulose. On the day following the last medication, the rats were killed and the thymus and adrenal of each rat were removed, cleaned, and weighed. Body weights and food consumptions were also recorded.

Anti-inflammatory Activity (α-tocopherol pouch test):

Male rats which weighed 120 g were selected for testing. A rapid subcutaneous injection of 25 mL of air was made between the scapulae of each rat. This resulted in the establishment of an airfilled pouch into which 0.5 mL of dl-α-tocopherol was injected. The test compound was administered in daily oral doses for 7 days beginning on the day of pouch formation. The compound to be tested was suspended in 1% gum tragacanth. Twenty-four hours after the last medication, the pouches were dissected free, and the fluid volume was measured. The inhibition of liquid exudate is a measure of the anti-inflammatory activity.

Glycogenic Activity:

Mature male rats were bilaterally adrenalectomized 5 days prior to the test. These rats were medicated orally with the test compound for 5 days. Seven hours after the last medication, the rats (which have been fasted overnight) were anesthetized with sodium pentobarbital and a portion of one lobe of the liver was removed and frozen on dry ice for subsequent glycogen determination.

Cotton Pellet Granuloma Assay for Locally Administered Anti-inflammatory Compounds [modification of method of Hershberger et al., Endocrinology 60, 153 (1957)]:

Cotton pellets weighing 20 to 29 mgs were impregnated with the test agent dissolved and/or suspended in 0.2 ml of absolute ethanol and air dried. The impregnated pellets were then implanted subcutaneously in the dorsal region of 200 to 220 g male rats. Seven days after implantation the animals were sedated and the adrenals, thymus and pellets were removed and weighed. The pellets also were dried to a constant weight by heating to 70° C. for 24 hours under vacuum.

The compounds of the invention can be formulated for topical application by solution or dispersion in a conventional pharmaceutically acceptable liquid, cream or ointment base. The effective ingredient is preferably present in a concentration of 0.01% to 5.0% by weight.

The compounds of the invention can be formulated for oral administration in tablet or capsule form with conventional excipients. The active ingredient is preferably present in an amount of 1 mg to 100 mg per unit dosage form.

The following examples will further illustrate the invention.

EXAMPLE 1

(a)

5-Ethenyl-3-hydroxymethylene-4,4a,7,8-tetrahydro-4a-methyl-2(3H)-naphthalenone

A solution of 50.0 g (0.265 mol) of 5-ethenyl-4,4a,7,8-tetrahydro-4a-methyl-2(3H)-naphthalenone in 350 mL of tetrahydrofuran was cooled to −5° C. in an ice-methanol bath and stirred under nitrogen while 57.2 g (1.06 mol) of sodium methoxide was added. The resulting mixture was stirred for 30 min at −5° C. and then a solution of 114 mL (1.85 mol) of methyl formate in 100 mL of tetrahydrofuran was added slowly. The mixture was stirred overnight at room temperature and then poured onto a mixture of ice-water (1500 mL) and 6 N hydrochloric acid (265 mL). The product was extracted with ether and the combined extracts were washed with water. The dried extract was dried over anhydrous magnesium sulfate and concentrated in vacuo to afford an oil. This oil was triturated with hexane (4×250 mL) and the combined triturates were dried over magnesium sulfate and concentrated in vacuo to afford 55.37 g of a red oil, consisting essentially of the above-entitled compound as established by proton NMR (PMR) spectral data.

(b)
1-Ethenyl-6-(4-fluorophenyl)-3,4,9,9a-tetrahydro-9a-methyl-6H-naphtho[2,3-c]pyrazole (II; R'=F)

4-Fluorophenylhydrazine hydrochloride (45.85 g, 0.282 mol) and sodium acetate (23.14 g, 0.282 mol) were added to a solution of 55.37 g (0.256 mol) of the product obtained in part (a) above in 225 mL of glacial acetic acid. The mixture was stirred overnight at room temperature and then concentrated in vacuo to afford a semi-solid. This material was suspended in ether (1 L) and filtered to remove sodium chloride. The ether filtrate was washed with water (4×250 mL), saturated sodium bicarbonate (until weakly basic) and saturated sodium chloride (100 mL). The extract was dried over anhydrous magnesium sulfate, decolorized with charcoal and concentrated in vacuo to afford an oil. This oil was triturated with 1:2 ether-hexane (3×750 mL) to afford 69.58 g of a dark brown oil. An analytical sample was prepared by using high-performance liquid chromatography with 1:3 ether-hexane as solvent. The resulting yellow oil was triturated with pentane to afford 1-ethenyl-6-(4-fluorophenyl)-3,4,9,9a-tetrahydro-9a-methyl-6H-naphtho[2,3-c]pyrazole as a yellow solid, m.p. 70°-72° C., with a consistent PMR spectrum.

(c)
8-(4-Fluorophenyl)-4a,5,6,8,11,11a-hexahydro-11a-methylspiro[[1]-benzopyrano[5,6-f]indazole-3(2H),5'(2'H)-pyrimidine]-2',4',6'(1'H,3'H)trione (I; R=H, R'=F).

A mixture of 15.3 g (0.05 mol) of 1-ethenyl-6-(4-fluorophenyl)-3,4,9,9a-tetrahydro-9a-methyl-6H-naphtho[2,3-c]pyrazole (II) and 8.0 g (0.05 mol) of (1H,3H)-pyrimidine-2,4,5,6-tetrone in 150 mL of toluene was refluxed in an apparatus fitted with a Dean-Stark trap for 24 hours to remove water. The mixture was cooled to room temperature, and filtered to afford 21.55 g of a green solid. The green solid was recrystallized from EtOH to give 12.33 g of I (R=H, R'=F) as a grey solid, m.p. 235°-236° C. The proton NMR spectrum (PMR) was consistent with the assigned structure.

In the endocrine profile determination, the compound of formula I (R=H, R'=F) at a dose level of 5 mg/kg caused a 72% reduction in thymus weight, a 30% reduction in adrenal weight and 140% reduction in body weight gain as compared with the controls. In the α-tocopherol pouch test, the compound was active at $ED_{50}=4$ mg/kg. In the glycogenic activity test the compound at dose levels of 2.5 and 7.5 mg/kg/day×5 produced liver glycogen deposition values of 22.5±2.1 and 31.5±3.0 mg/g of tissue, respectively, as compared to 1.98±0.07 mg/g for the vehicle (1% gum tragacanth) alone.

EXAMPLE 2
8-(4-Fluorophenyl)-4a,5,6,8,11,11a-hexahydro-11a,1',3'-trimethylspiro[[1]-benzopyrano[5,6-f]indazole-3(2H),5'(2'H)-pyrimidine]-2',4',6'(1'H,3'H)trione (I; R=CH₃, R'=F)

To a suspension of 1.58 g (0.066 mol) of sodium hydride (previously washed with pentane and dried under a stream of nitrogen) in 200 mL dimethylformamide at 0° C. under nitrogen was slowly added 13.4 g (0.03 mol) of I (R=H, R'=F) (Example 1c) in 130 mL dimethylformamide. The reaction mixture was stirred at room temperature for 2 hours under nitrogen. Then 4.11 mL (0.066 mol) of methyl iodide was added slowly and reaction mixture stirred at room temperature overnight. The reaction mixture was poured into water (800 mL) to afford a solid which was isolated by filtration, washed with water, and air dried to afford 9.36 g of a solid. This solid was dissolved in an ether-chloroform mixture, filtered through silica gel, and the solvent removed in vacuo to afford a foam. The foam was crystallized from ether to give I (R=CH₃, R'=F), an off-white solid, m.p. 188°-189° C. The PMR spectrum was consistent with the assigned structure.

In the endocrine profile determination, the compound of formula I (R=CH₃, R'=F) at a dose level of 0.2 mg/kg caused a 28% reduction in thymus weight, a 25% reduction in adrenal weight and 65% reduction in body weight gain as compared with the controls. At a dose level of 1 mg/kg the percent reductions were 71 (thymus), 57 (adrenals) and 127 (body weight gain). In the α-tocopherol pouch test, the compound was active at $ED_{50}=2$ mg/kg. In the glycogenic activity test the compound at dose levels of 3 and 9 mg/kg/day×5 produced liver glycogen deposition values of 17.5±2.1 and 60.9±2.3 mg/g of tissue, respectively, as compared with 2.2±0.1 mg/g for the vehicle.

The following compounds were prepared following the procedure of Example 2 while substituting the appropriate alkylating agent for the methyl iodide of that Example.

EXAMPLE 3
8-(4-Fluorophenyl)-4a,5,6,8,11,11a-hexahydro-11a-methyl-1',3'-(2-propyl)spiro[[1]-benzopyrano[5,6-f]indazole-3(2H),5'(2'H)-pyrimidine]-2',4',6'(1'H,3'H)trione (I; R=CH₂C≡CH, R'=F)

This compound was obtained in 37% yield as a yellow powder, m.p. 109°-111° C. when crystallized from chloroform. It caused a 41% inhibition of liquid exudate formation in the α-tocopherol pouch test at a dose level of 29 mg/kg.

EXAMPLE 4
1',3'-Diethyl-8-(4-fluorophenyl)-4a,5,6,8,11,11a-hexahydro-11a-methylspiro[[1]-benzopyrano[5,6-f]indazole-3(2H),5'(2'H)-pyrimidine]-2',4',6'(1'H,3'H)trione (I; R=CH₂CH₃, R'=F)

This compound was obtained in 48% yield as a colorless powder, m.p. 171°-172° C. when crystallized from a methylene dichloride-heptane mixture. In the endocrine profile determination, the compound at a dose level of 100 mg/kg caused a 34% reduction in thymus weight, a 45% reduction in adrenal weight and 75% reduction in body weight gain as compared with the controls. The compound was inactive in the α-tocopherol pouch test at a dose level of 25 mg/kg.

EXAMPLE 5
8-(4-Fluorophenyl)-4a,5,6,8,11,11a-hexahydro-11a-methyl-1',3'-di-(2-propenyl)spiro[[1]-benzopyrano[5,6-f]indazole-3(2H),5'(2'H)-pyrimidine]-2',4',6'(1'H,3'H)trione (I; R=CH₂CH=CH₂, R'=F)

This compound was obtained in 37% yield as a colorless powder, m.p. 70°-72° C. when crystallized from ether. In the endocrine profile determination, the compound at a dose level of 50 mg/kg caused a 34% reduction in thymus weight, a 37% reduction in adrenal weight and 58% reduction in body weight gain as compared with the controls. The compound was inactive in the α-tocopherol pouch test at a dose level of 48 mg/kg.

EXAMPLE 6

(a)
1-Ethenyl-6-phenyl-3,4,9,9a-tetrahydro-9a-methyl-6H-naphtho[2,3-c]pyrazole (II; R'=H)

A mixture of 17.92 g of 5-ethenyl-4,4a,7,8-tetrahydro-4a-methyl-2(3H)-naphthalenone (Example 1a), 13.2 g of phenylhydrazine hydrochloride and 7.49 g of sodium acetate in 100 ml of glacial acetic acid was stirred at room temperature overnight. The mixture was then concentrated in vacuo, diluted with about 400 ml of methylene dichloride and filtered to remove sodium chloride. The filtrate was washed with water, saturated sodium bicarbonate solution (until weakly basic) and saturated sodium chloride solution, and dried over anhydrous magnesium sulfate with activated carbon added. The suspension was filtered and concentrated to an oil, which was triturated with 250 ml of ether and 300 ml of hexane, decanted and triturated again with ether and hexane. The combined extracts were filtered through a pad of magnesium sulfate and concentrated to a brown oil, 19.09 g of II (R'=H) with PMR spectrum consistent with the assigned structure.

(b) 4a,5,6,8,11,11a-Hexahydro-11a-methyl-8-phenyl-spiro[[1]-benzopyrano[5,6-f]indazole-3(2H),5'(2'H)-pyrimidine]-2',4',6'(1'H,3'H)trione (I; R and R'=H), was prepared from 19.09 g of the product obtained in part (a) above and 10.56 g of (1H,3H)-pyrimidine-2,4,5,6-tetrone according to the procedure described in Example 1(c). The crude product was recrystallized from acetone to give 7.54 g of I (R and R'=H) as a tan powder, m.p. 253°–254° C. The PMR spectrum was consistent with the assigned structure.

The compound of formula I (R and R'=H) showed no systemic endocrinological activity, but when tested in the cotton pellet granuloma assay at a dose level of 5.0 mg it caused a 59% reduction in the dried pellet weights as compared with the controls, there being no change in the weights of the adrenals or thymus.

EXAMPLE 7

8-(4-Fluorophenyl)-4a,5,6,8,11,11a-hexahydro-11a-methyl-1',3'-dipropylspiro[[1]-benzopyrano[5,6-f]indazole-3(2H),5'(2'H)-pyrimidine]-2',4',6'(1'H,3'H)trione was prepared from 11 g of 8-(4-fluorophenyl)-4a,5,6,8,11,11a-hexahydro-11a-methylspiro[[1]-benzopyrano[5,6-f]indazole-3(2H),5'(2'H)-pyrimidine]-2',4',6'(1'H,3'H)trione (Example 1c) and 5.5 mL of n-propyl iodide in the presence of 2.69 g of sodium hydride in dimethylformamide according to the procedure of Example 2. The product was purified by preparative liquid chromatography to give the compound of formula I (R=CH₂CH₂CH₃, R'=F) as very pale green crystals, m.p. 81°–82° C.

The compound of formula I (R=CH₂CH₂CH₃, R'=F) showed no systemic endocrinological activity, but when tested in the cotton pellet granuloma assay at a dose level of 5.0 mg it caused a 35% reduction in the dried pellet weights as compared with the controls, there being no change in the weights of the adrenals or thymus.

We claim:
1. A compound having the formula:

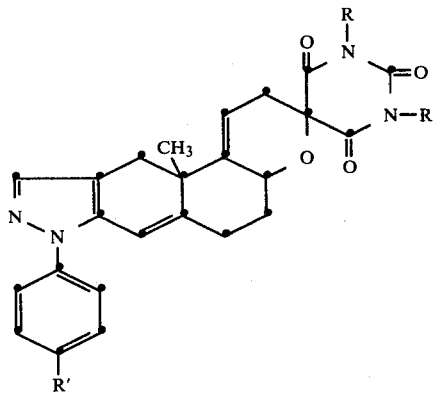

wherein R is selected from the group consisting of hydrogen, methyl, ethyl, propyl, 2-propenyl and 2-propynyl; and R' is selected from the group consisting of hydrogen and fluoro.

2. 8-(4-Fluorophenyl)-4a,5,6,8,11,11a-hexahydro-11a-methylspiro[[1]-benzopyrano[5,6-f]indazole-3(2H),5'(2'H)-pyrimidine]-2',4',6'(1'H,3'H)trione, according to claim 1.

3. 8-(4-Fluorophenyl)-4a,5,6,8,11,11a-hexahydro-11a,1',3'-trimethylspiro[[1]-benzopyrano[5,6-f]indazole-3(2H),5'(2'H)-pyrimidine]-2',4',6'(1'H,3'H)trione, according to claim 1.

4. 8-(4-Fluorophenyl)-4a,5,6,8,11,11a-hexahydro-11a-methyl-1',3'-(2-propynyl)spiro[[1]-benzopyrano[5,6-f]indazole-3(2H),5'(2'H)-pyrimidine]-2',4',6'(1'H,3'H)trione, according to claim 1.

5. 1',3'-Diethyl-8-(4-fluorophenyl)-4a,5,6,8,11,11a-hexahydro-11a-methylspiro[[1]-benzopyrano[5,6-f]indazole-3(2H),5'(2'H)-pyrimidine]-2',4',6'(1'H,3'H)trione, according to claim 1.

6. 8-(4-Fluorophenyl)-4a,5,6,8,11,11a-hexahydro-11a-methyl-1',3'-di-(2-propenyl)spiro[[1]-benzopyrano[5,6-f]indazole-3(2H),5'(2'H)-pyrimidine]-2',4',6'(1'H,3'H)trione, according to claim 1.

7. 4a,5,6,8,11,11a-Hexahydro-11a-methyl-8-phenyl-spiro[[1]-benzopyrano[5,6-f]indazole-3(2H),5'(2'H)-pyrimidine]-2',4',6'(1'H,3'H)trione, according to claim 1.

8. 8-(4-Fluorophenyl)-4a,5,6,8,11,11a-hexahydro-11a-methyl-1',3'-dipropylspiro[[1]-benzopyrano[5,6-f]indazole-3(2H),5'(2'H)-pyrimidine]-2',4',6'(1'H,3'H)trione, according to claim 1.

9. A process for preparing a compound according to claim 1 where R is H which comprises reacting 1-ethenyl-6-(4-R'-phenyl)-3,4,9,9a-tetrahydro-9a-methyl-6H-naphtho[2,3-c]pyrazole with (1H,3H)-pyrimidine-2,4,5,6-tetrone.

10. A process for preparing a compound according to claim 1, where R is other than hydrogen, which comprises reacting 1-ethenyl-6-(4-R'-phenyl)-3,4,9,9a-tetrahydro-9a-methyl-6H-naphtho[2,3-c]pyrazole with (1H,3H)-pyrimidine-2,4,5,6-tetrone, and reacting the resulting compound according to claim 1 where R is hydrogen with an alkylating agent of the formula R-X where R is other than hydrogen and X is halogen in the presence of a strong base.

11. A pharmaceutical composition for treating inflammation in mammals which comprises an antiinflammatorily effective amount of a compound according to claim 1 and a pharmaceutically acceptable carrier.

12. A method of reducing inflammation in a mammal which comprises administering to said mammal an antiinflammatorily effective amount of a composition according to claim 11.

* * * * *

UNITED STATES PATENT AND TRADEMARK OFFICE
CERTIFICATE OF CORRECTION

PATENT NO. : 4,412,995

DATED : November 1, 1983

INVENTOR(S) : Malcolm R. Bell and John L. Herrmann, Jr.

It is certified that error appears in the above-identified patent and that said Letters Patent are hereby corrected as shown below:

Column 6, line 33, "(2-propyl)" should read --(2-propynyl)--.

Signed and Sealed this

Twenty-fourth Day of January 1984

[SEAL]

Attest:

GERALD J. MOSSINGHOFF

Attesting Officer

Commissioner of Patents and Trademarks